(12) United States Patent
Chandra et al.

(10) Patent No.: US 7,204,464 B2
(45) Date of Patent: Apr. 17, 2007

(54) MEDICAL WIRE HOLDER

(75) Inventors: Charlie Chandra, San Jose, CA (US); Ari Ryan, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 87 days.

(21) Appl. No.: 11/040,505

(22) Filed: Jan. 21, 2005

(65) Prior Publication Data

US 2006/0163436 A1 Jul. 27, 2006

(51) Int. Cl.
*A47G 1/17* (2006.01)
(52) U.S. Cl. .......... 248/205.3; 248/74.3; 128/DIG. 26; 336/92; 24/303
(58) Field of Classification Search ............ 248/205.3, 248/74.3, 75; 24/303; 292/251.5; 174/135, 174/138 F, 71 R, 72 A, 92; 604/174; 128/DIG. 26; 335/302, 303; 336/92
See application file for complete search history.

(56) References Cited

U.S. PATENT DOCUMENTS

| | | | |
|---|---|---|---|
| 3,278,674 A * | 10/1966 | Chickvary et al. ....... | 174/138 F |
| 3,468,576 A * | 9/1969 | Beyer et al. ............ | 292/251.5 |
| 3,472,230 A | 10/1969 | Fogarty | |
| 3,592,186 A | 7/1971 | Oster | |
| 3,683,904 A | 8/1972 | Forster | |
| 3,822,906 A * | 7/1974 | Gaines .................... | 292/251.5 |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,336,806 A * | 6/1982 | Eldridge, Jr. ............... | 604/174 |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Korie Chan
(74) *Attorney, Agent, or Firm*—Crompton, Seager & Tufte LLC

(57) ABSTRACT

A device can easily and releasably secure a medical wire such as a guidewire or a filter wire. In some instances, such a device can include a wire holding device that may be considered to be disposable. A wire holding device may include a base fixture, a clamp fixture, holding apparatus to hold the clamp fixture to the base fixture, releasing apparatus to release the clamp fixture from the base fixture, and selecting apparatus to select between the holding apparatus and the releasing apparatus.

13 Claims, 6 Drawing Sheets

U.S. PATENT DOCUMENTS

| | | | |
|---|---|---|---|
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,886,061 A | 12/1989 | Fischelle et al. |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Giffort, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,269,759 A | 12/1993 | Hernandez et al. |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,361,962 A | 11/1994 | Andersen et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,464,023 A | 11/1995 | Viera |
| 5,476,104 A | 12/1995 | Sheahon |
| 5,484,418 A | 1/1996 | Quiachon et al. |
| 5,487,729 A | 1/1996 | Avellanet et al. |
| 5,507,767 A | 4/1996 | Maeda et al. |
| 5,512,044 A | 4/1996 | Duer |
| 5,520,656 A | 5/1996 | Byrd |
| 5,527,354 A | 6/1996 | Fontaine et al. |
| 5,536,242 A | 7/1996 | Willard et al. |
| 5,540,707 A | 7/1996 | Ressemann et al. |
| 5,542,938 A | 8/1996 | Avellanet et al. |
| 5,549,626 A | 8/1996 | Miller et al. |
| 5,555,893 A | 9/1996 | Hackett et al. |
| 5,558,101 A | 9/1996 | Brooks et al. |
| 5,562,724 A | 10/1996 | Vowerk et al. |
| 5,569,274 A | 10/1996 | Rapacki et al. |
| 5,569,275 A | 10/1996 | Kotula et al. |
| 5,570,701 A | 11/1996 | Ellis et al. |
| 5,579,779 A | 12/1996 | Humphrey |
| 5,588,442 A | 12/1996 | Scovil et al. |
| 5,606,980 A | 3/1997 | Calhoun et al. |
| 5,623,943 A | 4/1997 | Hackett et al. |
| 5,630,427 A | 5/1997 | Hastings |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,706,827 A | 1/1998 | Ehr et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,370 A | 5/1998 | Brooks et al. |
| 5,749,848 A | 5/1998 | Jang et al. |
| 5,769,816 A | 6/1998 | Barbut et al. |
| 5,776,080 A | 7/1998 | Thome et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |

| | | | | | | |
|---|---|---|---|---|---|---|
| 5,833,650 | A | 11/1998 | Imran | 6,245,089 | B1 | 6/2001 | Daniel et al. |
| 5,846,260 | A | 12/1998 | Maahs | 6,258,115 | B1 | 7/2001 | Dubrul |
| 5,848,964 | A | 12/1998 | Samuels | 6,264,663 | B1 | 7/2001 | Cano |
| 5,876,367 | A | 3/1999 | Kaganov et al. | 6,264,672 | B1 | 7/2001 | Fisher |
| 5,893,867 | A | 4/1999 | Bagaoisan et al. | 6,270,513 | B1 | 8/2001 | Tsugita et al. |
| 5,895,399 | A | 4/1999 | Barbut et al. | 6,277,138 | B1 | 8/2001 | Levinson et al. |
| 5,902,263 | A | 5/1999 | Patterson et al. | 6,277,139 | B1 | 8/2001 | Levinson et al. |
| 5,906,618 | A | 5/1999 | Larson, III | 6,280,413 | B1 | 8/2001 | Clark et al. |
| 5,908,435 | A | 6/1999 | Samuels | 6,287,321 | B1 | 9/2001 | Jang |
| 5,910,154 | A | 6/1999 | Tsugita et al. | 6,290,710 | B1 | 9/2001 | Cryer et al. |
| 5,911,734 | A | 6/1999 | Tsugita et al. | 6,309,399 | B1 | 10/2001 | Barbut et al. |
| 5,916,193 | A | 6/1999 | Stevens et al. | 6,319,268 | B1 | 11/2001 | Ambrisco et al. |
| 5,925,016 | A | 7/1999 | Chornenky et al. | 6,344,049 | B1 | 2/2002 | Levinson et al. |
| 5,925,060 | A | 7/1999 | Forber | 6,471,172 | B1 | 10/2002 | Lemke et al. |
| 5,925,062 | A | 7/1999 | Purdy | 6,559,748 | B1 * | 5/2003 | Nakano .................. 336/176 |
| 5,925,063 | A | 7/1999 | Khosravi | 6,656,199 | B1 | 12/2003 | Lafontaine |
| 5,928,203 | A | 7/1999 | Davey et al. | 6,746,466 | B2 | 6/2004 | Eidenschink et al. |
| 5,928,218 | A | 7/1999 | Gelbfish | 6,827,722 | B1 | 12/2004 | Schoenefeld |
| 5,934,284 | A | 8/1999 | Plaia et al. | 6,971,147 | B2 * | 12/2005 | Halstead .................. 24/303 |
| 5,935,139 | A | 8/1999 | Bates | 2002/0087100 | A1 | 7/2002 | Onuki et al. |
| 5,938,645 | A | 8/1999 | Gordon | 2002/0165484 | A1 | 11/2002 | Bowe et al. |
| 5,941,869 | A | 8/1999 | Patterson et al. | 2004/0006329 | A1 | 1/2004 | Scheu |
| 5,941,896 | A | 8/1999 | Kerr | 2004/0199197 | A1 | 10/2004 | Eidenschink et al. |
| 5,947,995 | A | 9/1999 | Samuels | | | | |
| 5,951,585 | A | 9/1999 | Cathcart et al. | FOREIGN PATENT DOCUMENTS | | | |
| 5,954,745 | A | 9/1999 | Gertler et al. | DE | 34 17 738 | | 11/1985 |
| 5,976,172 | A | 11/1999 | Homsma et al. | DE | 40 30 998 A1 | | 10/1990 |
| 5,980,555 | A | 11/1999 | Barbut et al. | EP | 0 200 688 | | 11/1986 |
| 5,989,210 | A | 11/1999 | Morris et al. | EP | 0 293 605 A1 | | 12/1988 |
| 5,989,271 | A | 11/1999 | Bonnette et al. | EP | 0356630 A1 | | 7/1990 |
| 5,989,281 | A | 11/1999 | Barbut et al. | EP | 0 411 118 A1 | | 2/1991 |
| 5,993,469 | A | 11/1999 | McKenzie et al. | EP | 0 427 429 A2 | | 5/1991 |
| 5,997,557 | A | 12/1999 | Barbut et al. | EP | 0 437 121 B1 | | 7/1991 |
| 6,001,118 | A | 12/1999 | Daniel et al. | EP | 0 472 334 A1 | | 2/1992 |
| 6,007,557 | A | 12/1999 | Ambrisco et al. | EP | 0 472 368 A2 | | 2/1992 |
| 6,010,522 | A | 1/2000 | Barbut et al. | EP | 0 533 511 A1 | | 3/1993 |
| 6,013,038 | A | 1/2000 | Pflueger | EP | 0 655 228 A1 | | 11/1994 |
| 6,013,085 | A | 1/2000 | Howard | EP | 0 686 379 A2 | | 6/1995 |
| 6,027,520 | A | 2/2000 | Tsugita et al. | EP | 0 696 447 A2 | | 2/1996 |
| 6,042,598 | A | 3/2000 | Tsugita et al. | EP | 0 737 450 A1 | | 10/1996 |
| 6,051,014 | A | 4/2000 | Jang | EP | 0 743 046 A1 | | 11/1996 |
| 6,051,015 | A | 4/2000 | Maahs | EP | 0 759 287 A1 | | 2/1997 |
| 6,053,932 | A | 4/2000 | Daniel et al. | EP | 0 771 549 A2 | | 5/1997 |
| 6,059,814 | A | 5/2000 | Ladd | EP | 0 784 988 A1 | | 7/1997 |
| 6,066,149 | A | 5/2000 | Samson et al. | EP | 0 852 132 A1 | | 7/1998 |
| 6,066,158 | A | 5/2000 | Engelson et al. | EP | 0 934 729 | | 8/1999 |
| 6,068,645 | A | 5/2000 | Tu | FR | 2 580 504 | | 10/1986 |
| 6,086,605 | A | 7/2000 | Barbut et al. | FR | 2 643 250 A1 | | 8/1990 |
| 6,117,154 | A | 9/2000 | Barbut et al. | FR | 2 666 980 | | 3/1992 |
| 6,129,739 | A | 10/2000 | Khosravi | FR | 2 768 326 A1 | | 3/1999 |
| 6,136,016 | A | 10/2000 | Barbut et al. | GB | 2 020 557 B | | 1/1983 |
| 6,142,987 | A | 11/2000 | Tsugita | JP | 8-187294 A | | 7/1996 |
| 6,144,277 | A * | 11/2000 | Matsui et al. .................. 336/92 | JP | 08257134 | | 10/1996 |
| 6,152,946 | A | 11/2000 | Broome et al. | JP | 09253217 | | 9/1997 |
| 6,165,200 | A | 12/2000 | Tsugita et al. | SU | 764684 | | 9/1980 |
| 6,168,579 | B1 | 1/2001 | Tsugita | WO | WO 88/09683 | | 12/1988 |
| 6,171,327 | B1 | 1/2001 | Daniel et al. | WO | WO 92/03097 | | 3/1992 |
| 6,171,328 | B1 | 1/2001 | Addis | WO | WO 94/14389 | | 7/1994 |
| 6,179,851 | B1 | 1/2001 | Barbut et al. | WO | WO 94/24946 | | 11/1994 |
| 6,179,859 | B1 | 1/2001 | Bates et al. | WO | WO 96/01591 | | 1/1996 |
| 6,179,861 | B1 | 1/2001 | Khosravi et al. | WO | WO 96/04875 A1 | | 2/1996 |
| 6,203,561 | B1 | 3/2001 | Ramee et al. | WO | WO 96/10375 | | 4/1996 |
| 6,206,868 | B1 | 3/2001 | Parodi | WO | WO 96/19941 | | 7/1996 |
| 6,214,026 | B1 | 4/2001 | Lepak et al. | WO | WO 96/23441 | | 8/1996 |
| 6,215,381 | B1 * | 4/2001 | Aoki .................. 335/207 | WO | WO 96/33677 | | 10/1996 |
| 6,221,006 | B1 | 4/2001 | Dubrul et al. | WO | WO 97/17100 | | 5/1997 |
| 6,224,620 | B1 | 5/2001 | Maahs | WO | WO 97/27808 | | 8/1997 |
| 6,231,544 | B1 | 5/2001 | Tsugita et al. | WO | WO 97/42879 | | 11/1997 |
| 6,235,044 | B1 | 5/2001 | Root et al. | WO | WO 98/02084 | | 1/1998 |
| 6,235,045 | B1 | 5/2001 | Barbut et al. | WO | WO 98/02112 | | 1/1998 |
| 6,238,412 | B1 | 5/2001 | Dubrul et al. | WO | WO 98/23322 | | 6/1998 |
| 6,245,087 | B1 | 6/2001 | Addis | WO | WO 98/33443 | | 8/1998 |
| 6,245,088 | B1 | 6/2001 | Lowery | | | | |

| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprothesis: A New Technique Using Nitinol Wire," *AJR*, pp. 261-263 (Apr. 1983).

Diethrich et al., "Percutaneous Techniques for Endoluminal Carotid Interventions,"*J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omincath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

MEDICAL WIRE HOLDER

TECHNICAL FIELD

The invention relates generally to devices configured to releasably hold a wire and more specifically to devices configured to releasably hold a medical wire such as a guidewire or a filter wire.

BACKGROUND

Heart and vascular disease are major problems in the United Sates and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic or narrowed blood vessels may be treated with a number of relatively non-invasive medical procedures including percutaneous transluminal angioplasty (PTA), percutaneous transluminal coronary angioplasty (PTCA), and atherectomy. These procedures typically include steps of advancing various treatment devices such as balloon catheters, atherectomy catheters, stent delivery catheters and the like over a wire such as a guidewire. In some instances, these devices are deployed over a filter wire, which can be considered to be a guidewire having a filter secured to the distal end thereof.

Often times when treating occluded, stenotic or narrowed blood vessels, one or more medical devices such as those noted above are advanced over a guidewire or filter wire that has previously been advanced to or even beyond a treatment site. One of the challenges faced by the physician or other health care professional in advancing devices over the wire is limiting or even preventing undesirable movement of the wire once the wire has been deployed. In some cases, the user will attempt to hold the wire immobile with one hand while advancing a device over the wire with the other hand.

Therefore, a need remains for a device that will easily and releasably secure a guidewire or filter wire once deployed, thereby freeing the physician or other health care professional to concentrate instead on advancing devices over the guidewire or filter wire.

SUMMARY

The present invention pertains to a device that easily and releasably secures a medical wire such as a guidewire or a filter wire. In some instances, the present invention pertains to a wire holding device that may be considered to be disposable.

Accordingly, an example embodiment of the present invention may be found in a disposable wire holder that is configured to releasable secure a medical wire. The disposable wire holder includes a base assembly and a top assembly. The base assembly includes a first magnet having a first polarity and a second magnet having a second polarity. The top assembly includes a magnet track that is disposed within the top assembly and a third magnet that is disposed within the magnet track. The third magnet is translatable between an open position in which the third magnet overlies the first magnet and a closed position in which the third magnet overlies the second magnet.

Another example embodiment of the present invention may be found in a medical wire clamp that includes a base fixture and a clamp fixture. The medical wire clamp can include holding apparatus to hold the clamp fixture against the base fixture, releasing apparatus to release the clamp fixture from the base fixture, and selecting apparatus to select between the holding apparatus and the releasing apparatus.

Another example embodiment of the present invention may be found in a method of using a medical wire clamp. The medical wire clamp may include a base fixture, a clamp fixture, holding apparatus to hold the clamp fixture against the base fixture, and releasing apparatus to release the clamp fixture from the base fixture. A medical wire having a proximal portion and a distal portion may be advanced to a treatment site. The distal portion of the medical wire may be positioned within the medical wire clamp, and the holding structure can be activated to hold the clamp fixture to the base fixture, thereby securing the medical wire.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
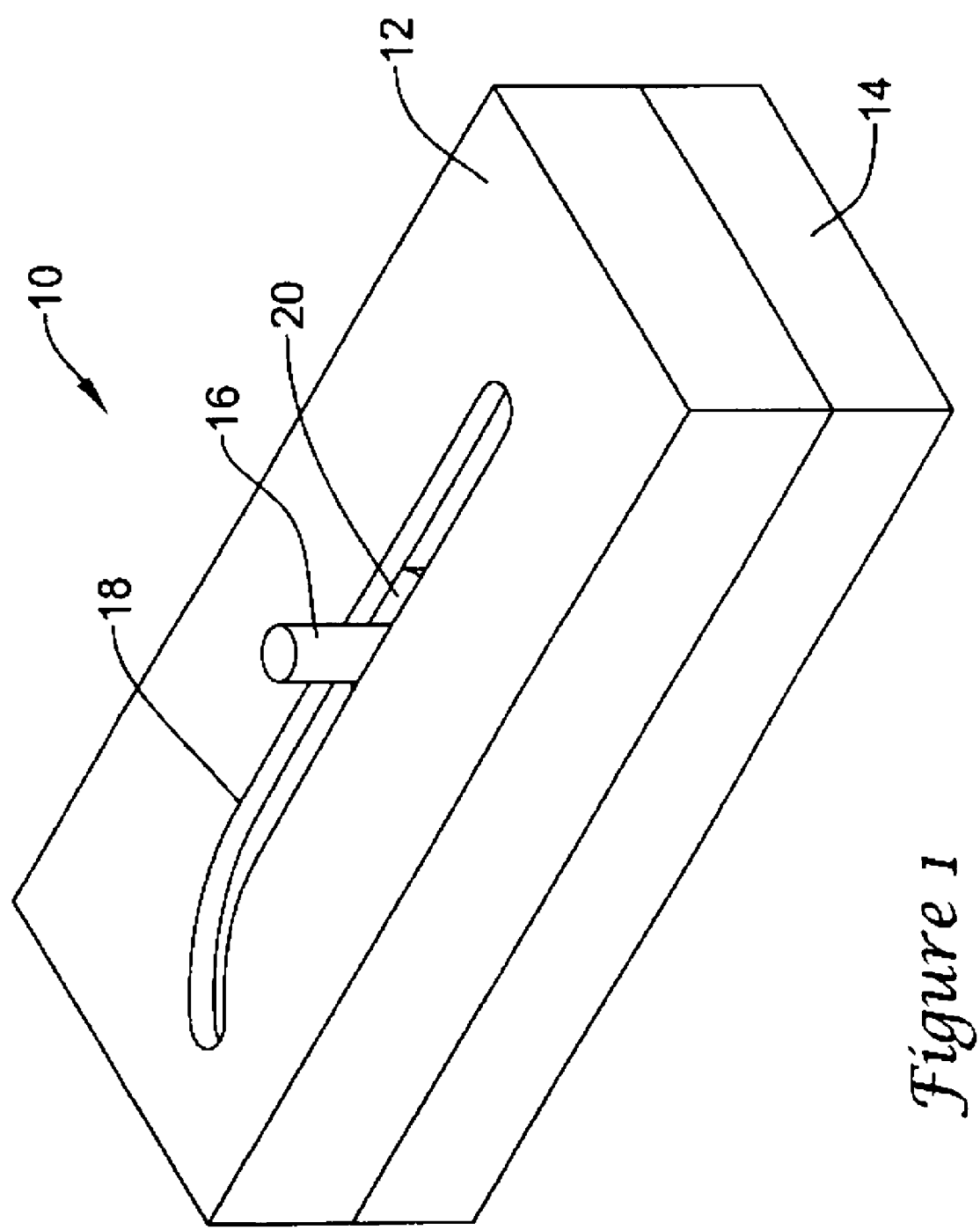
FIG. 1 is a perspective view of a medical wire holder in accordance with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value, i.e., having the same function or result. In many instances, the term "about" may include numbers that are rounded to the nearest significant figure.

The recitation of numerical ranges by endpoints includes all numbers within that range. For example, a range of 1 to 5 includes 1, 1.5, 2, 2.75, 3, 3.80, 4 and 5.

As used in this specification and in the appended claims, the singular forms "a", "an", and "the" include plural referents unless the content clearly dictates otherwise. As used in this specification and in the appended claims, the term "or" is generally employed in its sense including "and/or" unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a perspective view of a medical wire holder 10. The medical wire holder 10 includes a top portion 12 and a bottom portion 14. The top portion 12 may include a handle 16 that is disposed within a handle track 18. The handle 16 can be secured to a magnet 20 that is partially visible within the handle track 18. The handle 16 may be used to slide magnet 20 within a magnet track (not visible in this Figure) in order to either open or close the medical wire holder 10 as will be discussed in greater detail hereinafter. The handle 16 may be formed of any suitable metallic or polymeric material. In some instances, the handle 16 may be a cylindrical magnet that is secured to the magnet 20.

Figure 4:
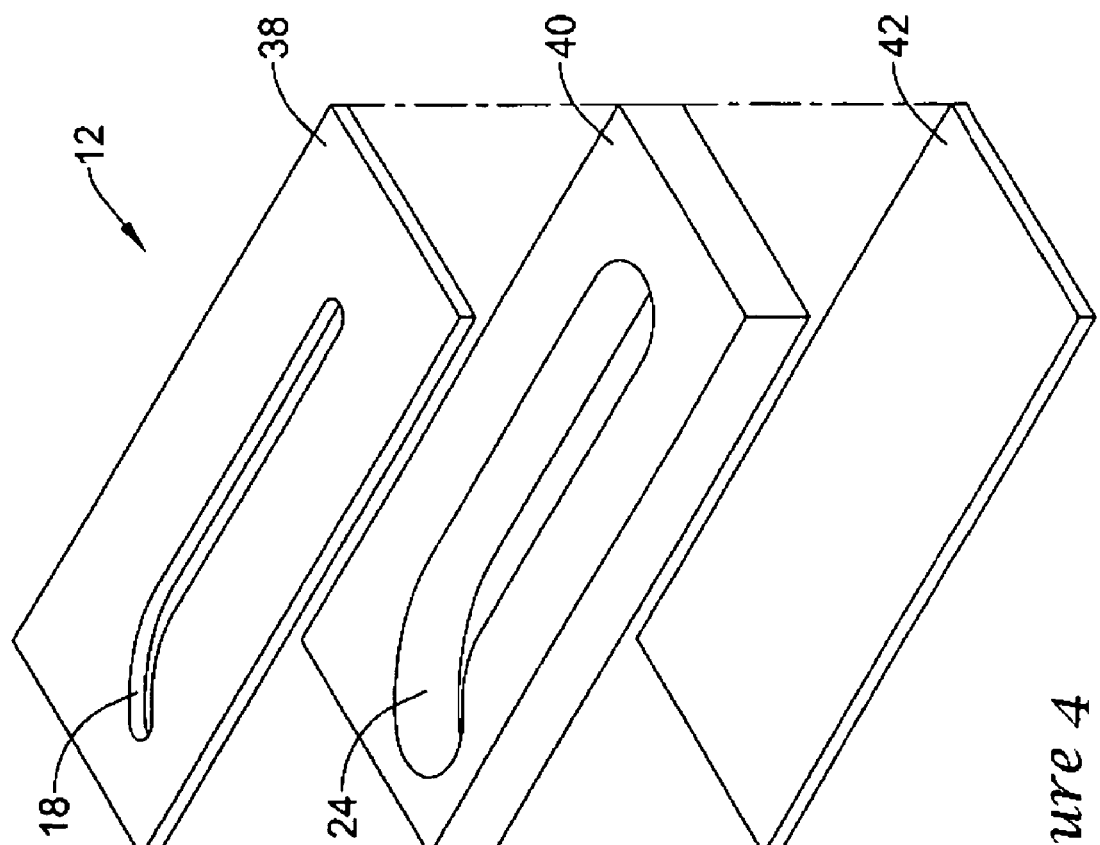
FIG. 4 is an exploded perspective view illustrating an embodiment of the top portion of the medical wire holder of FIG. 1.
Figure 5:
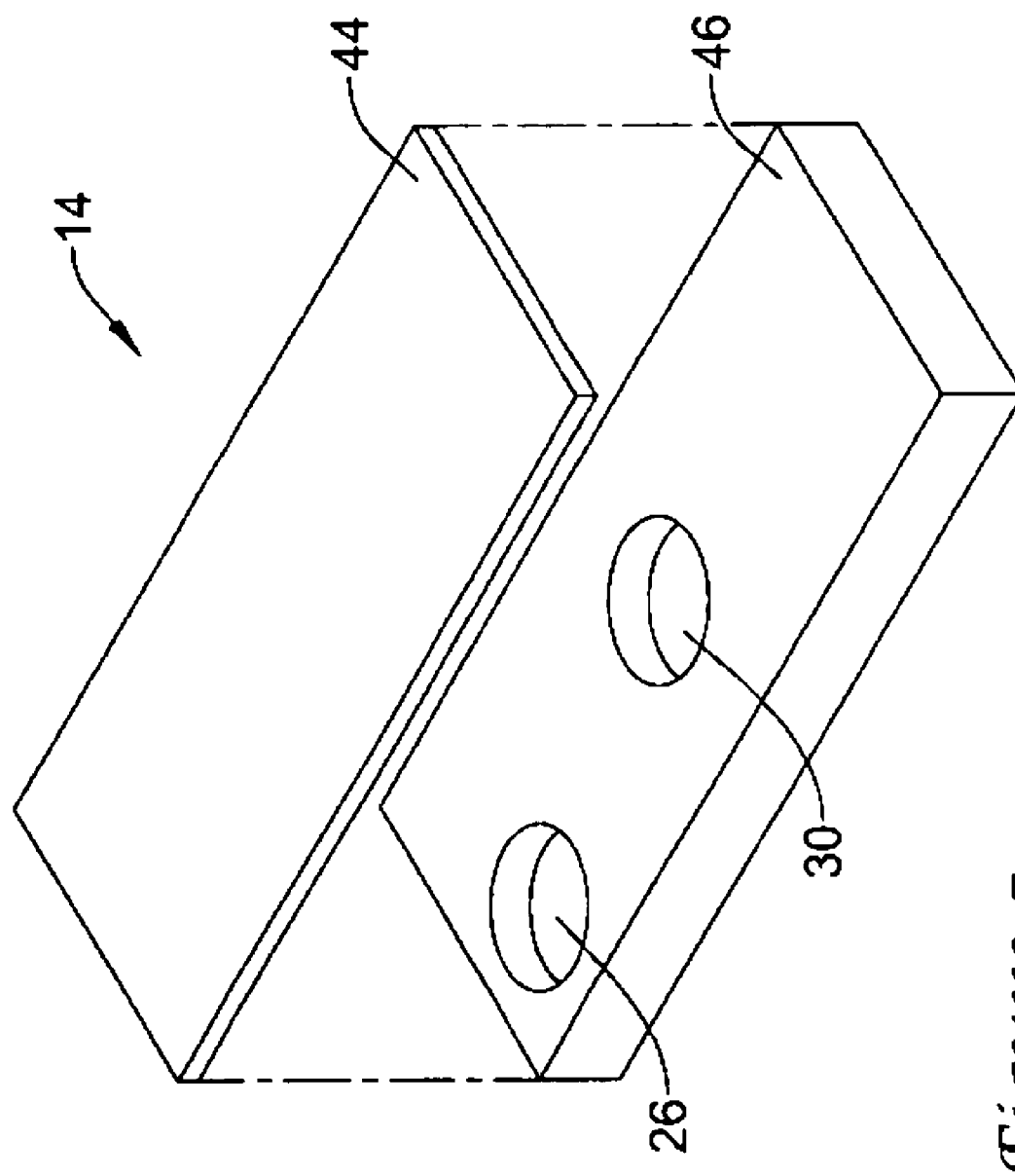
FIG. 5 is an exploded perspective view illustrating an embodiment of the bottom portion of the medical wire holder of FIG. 1.

The top portion 12 and the bottom portion 14 may each be formed of any suitable material. For ease of manufacturing and expense, the top portion 12 and the bottom portion 14 may be formed of any suitable polymeric material that is sufficiently strong and that is easily machineable. In some embodiments, the top portion 12 and the bottom portion 14 may be formed of a polycarbonate such as lexane. In some instances, the top portion 12 may be formed of a single block of lexane, and the features such as the handle track 18 and the magnet track may be drilled or otherwise formed within the single block of lexane. In other cases, such as illustrated in FIG. 4 (discussed later), the top portion 12 may be formed of several distinct layers of lexane. Similarly, the bottom portion 14 may be formed of a single block of a material such as lexane, or, as illustrated in FIG. 5, the bottom portion 14 may be formed of several distinct layers of lexane.

The medical wire holder 10 may be constructed to any suitable dimensions. In some instances, the medical wire holder 10 may have an overall length that is in the range of about 2" to about 6", an overall width that is in the range of about 1" to about 4", and an overall height (excluding the handle 18) that is in the range of about ½" to about 1⅝". In particular embodiments, the medical wire holder 10 can have an overall length of about three inches, an overall width of about one and one half inches, and a height (excluding the handle 18) that is about one inch or less. The handle 18 may have a height of about ½" and a diameter of about ⅛".

Figure 2:
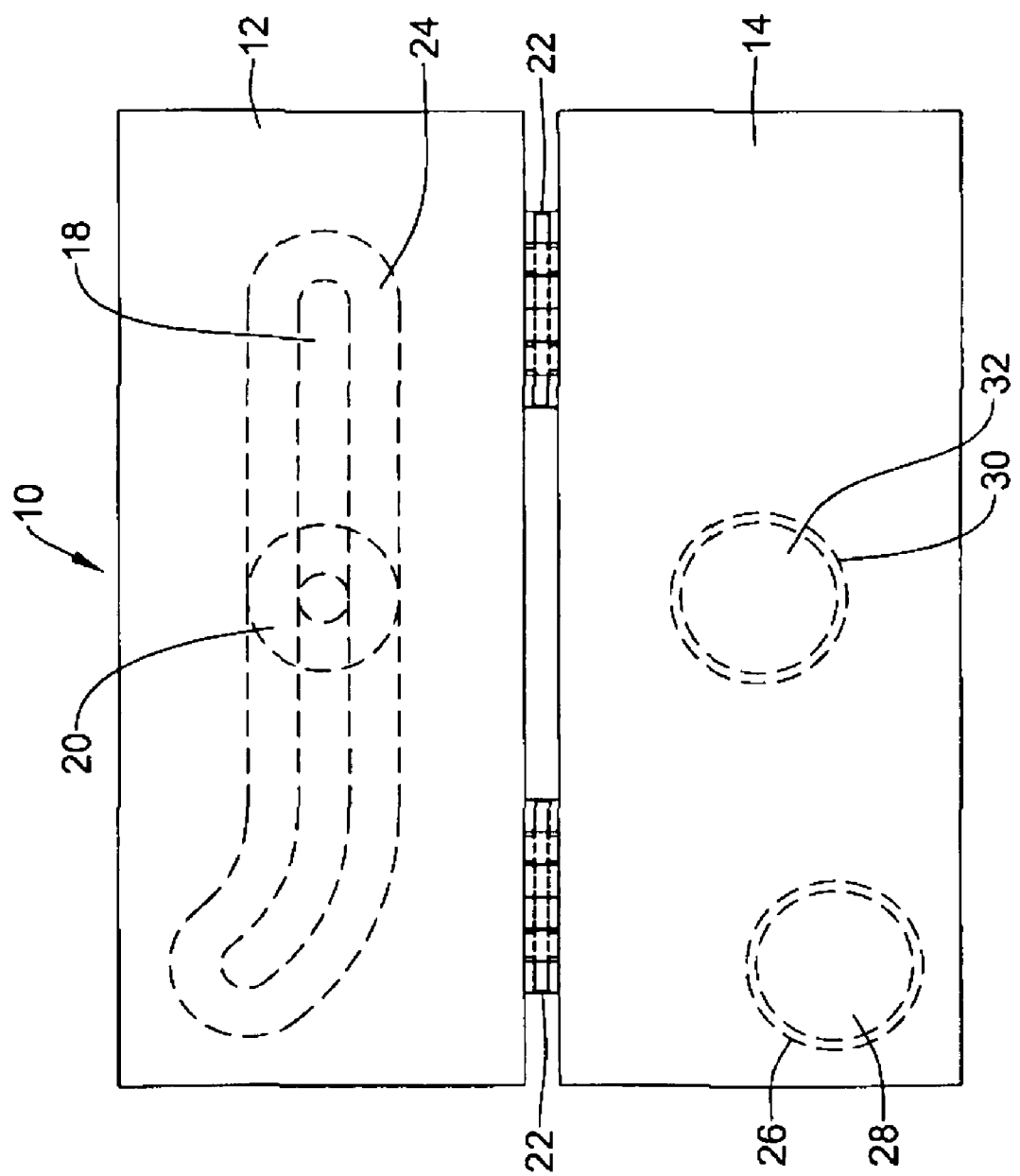
FIG. 2 is a partially phantom view of the medical wire holder of FIG. 1, shown in an open configuration.

In FIG. 2, the medical wire holder 10 has been opened to expose some of the internal structure of the top portion 12 and the bottom portion 14. In this embodiment, the top portion 12 and the bottom portion 14 are secured together along using two hinges 22. While two hinges 22 are illustrated, it should be noted that a single hinge (not shown) spanning substantially the length of the common edge of top and bottom portion 12 and 14 could be used. In some cases, common metallic hinges such as brass hinges may be used as hinges 22. In other cases, it is contemplated that a resilient material such as rubber could be used to join the top portion 12 to the bottom portion 14.

The top portion 12 can be seen to include, in phantom, the handle track 18 and a magnet track 24. Magnet 20 may be translated along the magnet track 24 by moving the handle 16. The bottom portion 14 can be seen to include, in phantom, an aperture 26 formed within the bottom portion 14 and a first magnet 28 disposed within the aperture 26. The bottom portion 14 also includes an aperture 30 formed within the bottom portion 14 and a second magnet 32 disposed within the aperture 30. As illustrated in FIG. 2, the magnet 20 can be translated along the magnet track 24 from a position in which the magnet 20 overlies the first magnet 28 to a position in which the magnet 20 overlies the second magnet 32. This refers, of course, to when the top portion 12 is disposed over the bottom portion 14, as seen for example in FIG. 1. For convenience, the magnet 20 will hereinafter be referred to as the third magnet 20.

The first magnet 28 and the second magnet 32 may be any suitable magnetic material. In some embodiments, the first magnet 28 and the second magnet 32 are each neodymium disc magnets and can be sized as appropriate. In particular embodiments, the first magnet 28 may be a neodymium disc magnet having a diameter of about ⅝ inches and a thickness of about ⅛ inches while the second magnet 32 may be a neodymium disc magnet having a diameter of about 9/16 inches and a thickness of about 3/16 inches. In some instances, the aperture 26 and the aperture 30 may be sized to accommodate the dimensions of the first magnet 28 and the second magnet 32, respectively.

A magnet such as a disc magnet can have one of two distinct and opposite polarities, depending on orientation. The top of a disc magnet may, to illustrate, have a North polarity while the bottom of a disc magnet would correspondingly have a South polarity. In some embodiments, the first magnet 28 can have a first polarity and the second magnet 32 can have a second polarity that is opposite the first polarity. The third magnet 20 may have a polarity equal to that of the first magnet 28. As a non-limiting example, the first magnet 28 may be installed within the aperture 26 having an orientation that provides a North polarity and the second magnet 32 may be installed within the aperture 30 having an orientation that provides a South polarity. In this particular example, the third magnet 20 would be oriented to have a North polarity.

When the third magnet 20 is positioned to overlie the first magnet 28, there will be a repulsive force between the first magnet 28 and the third magnet 20 due to both magnets being oriented to have a common polarity. When the third magnet 20 is positioned to overlie the second magnet 32, there will be an attractive force between the second magnet 32 and the third magnet 20 due to the magnets being oriented to have opposite polarities. Therefore, the medical wire holder 10 can be considered as having a closed position when the third magnet 20 overlies the second magnet 32 and an open position when the third magnet 20 overlies the first magnet 28.

When a medical wire such as a guidewire or a filter wire is placed between the top portion 12 and the bottom portion 14, the third magnet 20 may be translated along the magnet track 24 between the closed position and the open position. When the medical wire holder 10 is in the open position, the medical wire may easily be disposed within the medical wire holder 10. By moving the handle 16 (and hence the third magnet 20) along the magnet track 24 to a position in which the third magnet 20 overlies the second magnet 32, the medical wire holder 10 attains its closed position and the medical wire is securely held against movement.

Figure 3:
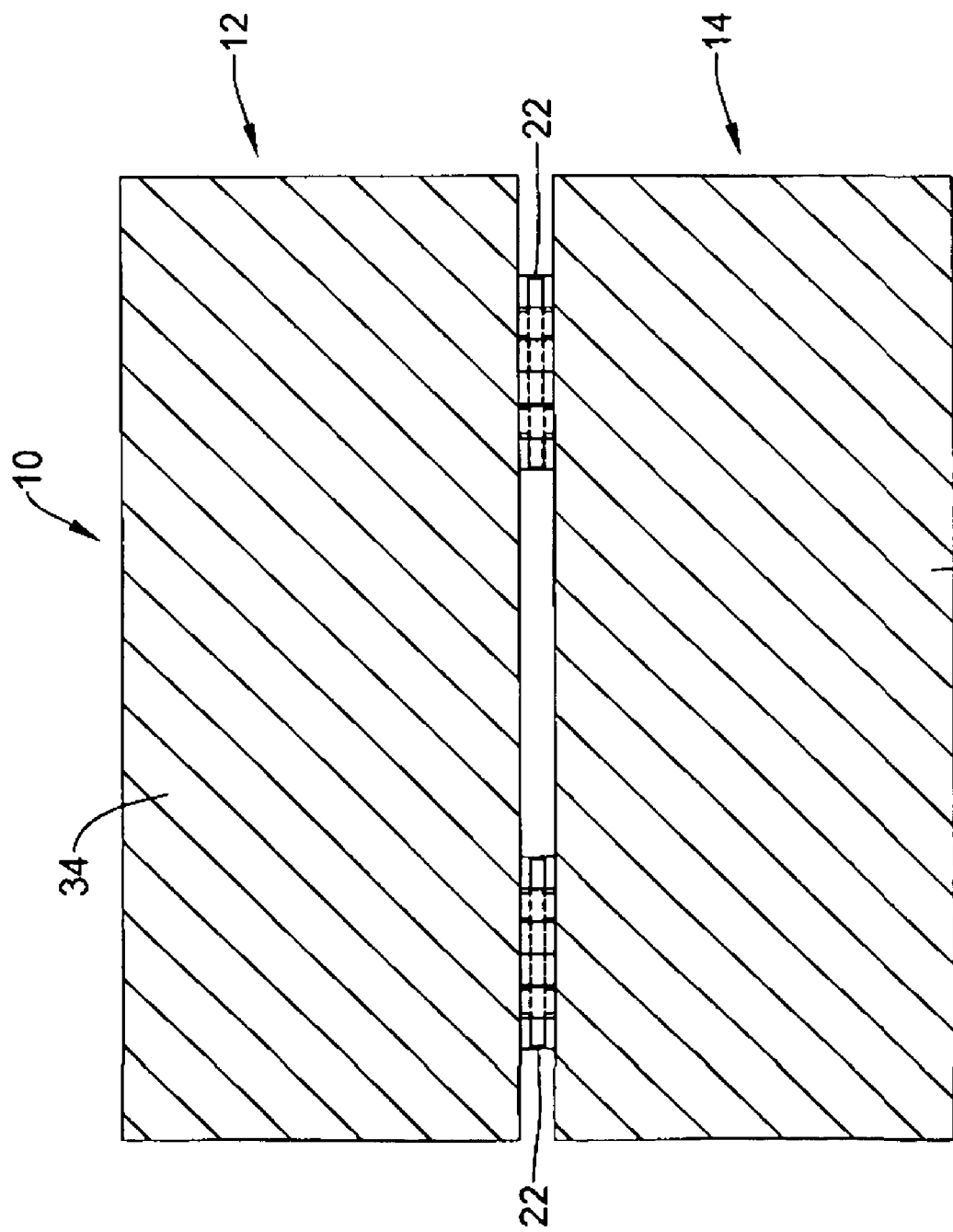
FIG. 3 is a view of the medical wire holder of FIG. 1, shown in an open configuration including wire gripping surfaces.

In some embodiments, a medical wire may be held in place by compressive forces between the top portion 12 and the bottom portion 14. In some embodiments, it may be useful to include a thin layer of a material on at least one of the top portion 12 and the bottom portion 14 to provide additional grip on a medical wire. In FIG. 3, for example, a thin layer 34 has been disposed over the top portion 12 while a thin layer 36 has been disposed over the bottom portion 14. Any suitable material may be used for thin layer 34 and for thin layer 36. In particular embodiments, rubber may be used.

In some embodiments, the thin layer 34 may be a thin layer of rubber that is glued or otherwise adhered to the top portion 12. The thin layer 36 may be a thin layer of rubber that is glued or otherwise adhered to the bottom portion 14. The thin layer 34 and the thin layer 36 may be distinct pieces of rubber. In some embodiments, however, the thin layer 34 and the thin layer 36 may be formed from a single thin piece of rubber that is secured to both top portion 12 and bottom portion 14. In this case, the rubber can provide a resilient material between the top portion 12 and the bottom portion 14 that may function as a hinge therebetween.

Turning now to FIG. 4, the construction of the top portion 12 is illustrated. In this embodiment, the top portion 12 is formed from a top piece 38, a middle piece 40, and a bottom piece 42. The top piece 38 can be formed of any suitable material such as lexane and can be drilled or otherwise machined to form the handle track 18. The handle track 18 may extend vertically the entire thickness of the top piece 38.

The middle piece 40 can be formed of any suitable material such as lexane and can be drilled or otherwise machined to form the magnet track 24. In some cases, the magnet track 24 extends vertically the entire thickness of the middle piece 40. In other cases, the magnet track 24 extends downwardly from an upper surface of the middle piece 40 to an internal point within the middle piece 40.

It will be appreciated that there are particular manufacturing advantages to forming the top portion 12 from three distinct pieces, as illustrated. Moreover, it can be seen that third magnet 20 can be positioned within and held captive within the magnet track 24.

Each of the top piece 38, the middle piece 40 and the bottom piece 42 may be constructed to any suitable dimensions. The overall length and width of each of the top piece 38, the middle piece 40 and the bottom piece 42 may be set according to the overall dimensions desired for medical wire holder 10, as discussed previously with respect to FIG. 1.

In some embodiments, the top piece 38 and the bottom piece 42 are relatively thinner, having a thickness that is in the range of about 1/32" to about 1/8". In particular embodiments, the top piece 38 and the bottom piece 42 are each about 1/16 inches thick. In some embodiments, the middle piece 40 can have a thickness that is in the range of about 3/16" to about 5/8". In particular embodiments, the middle piece 40 can have a thickness that is about 3/8 inches thick.

To assemble the top portion 12, the middle piece 40 may be glued or otherwise secured onto the bottom piece 42. An assembly including the third magnet 20 and the handle 16 may be positioned within the magnet track 24. The top piece 38 may then be glued or otherwise secured to the middle piece 40. Any suitable adhesive may be used. An example of an adhesive suitable for gluing polycarbonate materials together is Loctite® Plastix® Advanced Plalstic Bonder or Loctite® 4014 glue.

Turning now to FIG. 5, the construction of the bottom portion 16 is illustrated. In this embodiment, the bottom portion 14 is formed from an upper piece 44 and a lower piece 46. The lower piece 46 may be drilled or otherwise machined to form the aperture 26 and the aperture 30. In some cases, the aperture 26 and the aperture 30 are formed having a depth sufficient to accommodate the first magnet 28 and the second magnet 32, respectively, but do not extend all the way through the lower piece 46.

The upper piece 44 and the lower piece 46 may be formed of any suitable material such as lexane and can have any suitable dimensions. In some embodiments, the overall length and width of the upper piece 44 and the lower piece 46 are set according to the overall dimensions of the medical wire holder 10, as discussed previously with respect to FIG. 1.

In some embodiments, the upper piece 44 is relatively thinner and has a thickness that is in the range of about 1/32" to about 1/8". In particular embodiments, the upper piece 44 has a thickness that is about 1/16 inches thick. In some embodiments, the lower piece 46 is relatively thicker and has a thickness that is in the range of about 1/8" to about 1/2". In particular embodiments, the lower piece 46 has a thickness that is about 1/4 inches thick.

To assemble the bottom portion 14, the first magnet 28 and the second magnet 32 may be disposed within aperture 26 and aperture 30, respectively, of lower piece 46. The upper piece 44 may be glued or otherwise secured to the lower piece 46 using any suitable adhesive. An example of an adhesive suitable for gluing polycarbonate materials together is Loctite Plastix® Advanced Plalstic Bonder or Loctite® 4014 glue.

In an alternate embodiment, the bottom portion 14 may be formed of a single block of a suitable material such as lexane. In such an embodiment, the first magnet 28 may be glued or otherwise adhered in the aperture 26 while the second magnet 32 may be glued or otherwise adhered in the aperture 30. Inclusion of the thin layer 36 (FIG. 3) can also assist in holding the first magnet 28 and the second magnet 32 in position.

Figure 6:
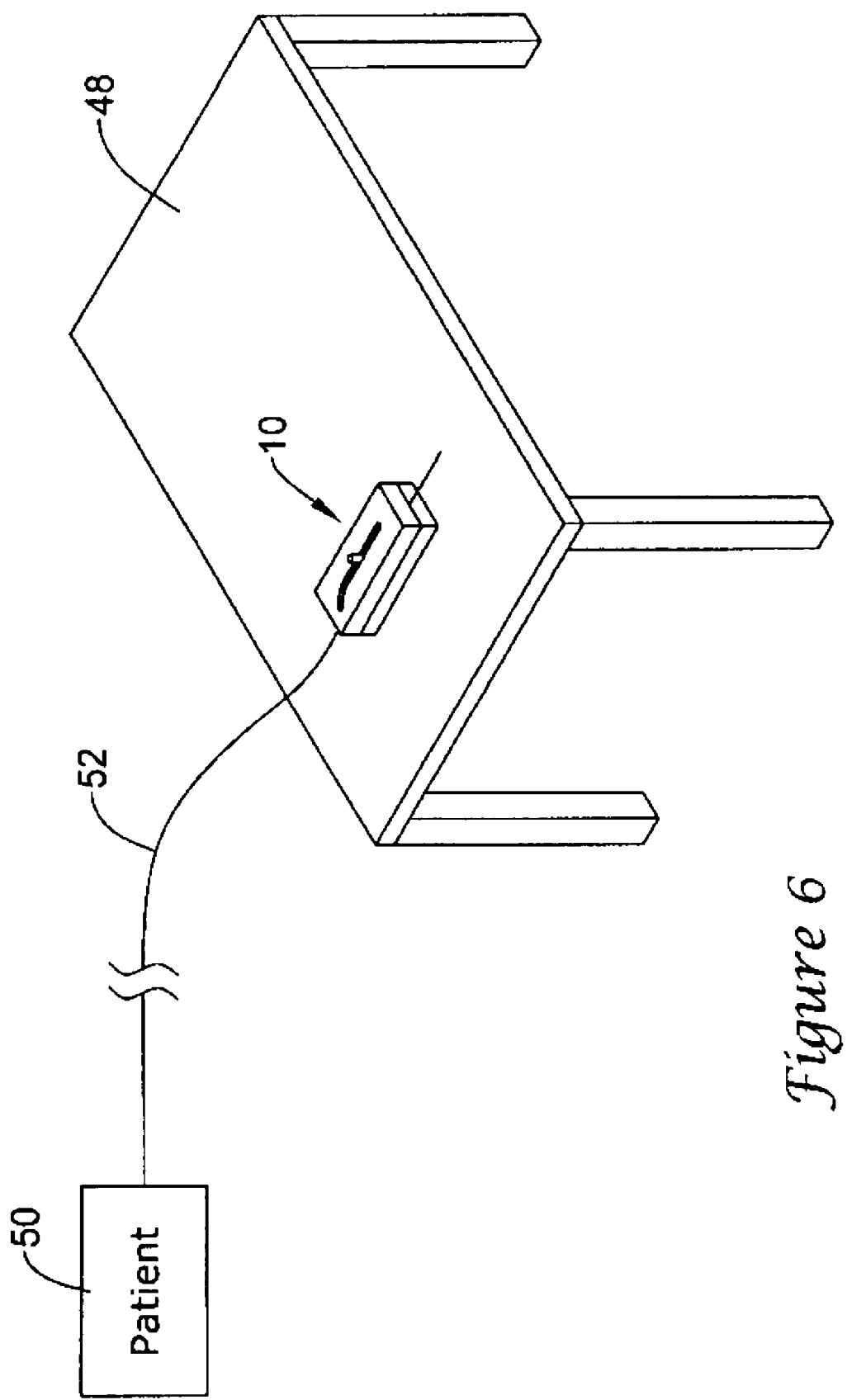
FIG. 6 is a schematic illustration of the medical wire holder of FIG. 1, in use.

Use of the medical wire holder 10 is illustrated in FIG. 6. In FIG. 6, the medical wire holder 10 has been fastened to a table 48. In this, the table 48 generically represents any suitable structure that may be present within a catheter lab or an operating room. The medical wire holder 10 may be fastened to the table 48 using double-face adhesive tape, hook and look fasteners, a pressure-sensitive adhesive placed on the bottom surface of the medical wire holder 10 and exposed by removing a protective layer, or any other suitable attachment mechanism.

A patient 50 is generically represented. Once the medical wire holder 10 has been secured to the table 48, a medical wire 52 may be advanced into and through the patient 50 as is known. The medical wire 52 may be a guidewire or a filter wire. Once the medical wire 52 has been properly positioned within the patient 50, the medical wire 52 may be positioned within the medical wire holder 10. The medical wire 52 can be secured by moving the medical wire holder 10 from its open position to its closed position. Any desired device may now be advanced over the medical wire 52.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

We claim:

1. A disposable wire holder configured to releasably secure a medical wire, the disposable wire holder comprising:
   a base assembly;
      a first magnet disposed within the base assembly, the first magnet having a first polarity;
      a second magnet disposed within the base assembly, the second magnet having a second polarity; and
      a first thin wire gripping layer comprising a resilient material secured to the base assembly; and
   a top assembly;
      a magnet track disposed within the top assembly;
      a second thin wire gripping layer secured to the top assembly; and
      a third magnet disposed within the magnet track, the third magnet translatable between an open position in which the third magnet overlies the first magnet and a closed position in which the third magnet overlies the second magnet.

2. The disposable wire holder of claim 1, wherein the top assembly releases from the base assembly when the third magnet is in the open position.

3. The disposable wire holder of claim 1, wherein the top assembly is secured to the base assembly when the third magnet is in the closed position.

4. The disposable wire holder of claim 1, wherein the third magnet has a polarity equal to the first polarity and opposite to the second polarity.

5. The disposable wire holder of claim 1, further comprising at least one hinge securing the top assembly to the base assembly.

6. The disposable wire holder of claim 1, wherein the first magnet comprises a neodymium magnet.

7. The disposable wire holder of claim 1, wherein the second magnet comprises a neodymium magnet.

8. The disposable wire holder of claim 1, wherein the third magnet comprises a neodymium magnet.

9. The disposable wire holder of claim 1, wherein the top assembly comprises a top layer, a middle layer and a bottom layer, where the magnet track is formed within the middle layer.

10. The disposable wire holder of claim 9, further comprising a handle track formed within the top layer and overlying the magnet track.

11. The disposable wire holder of claim 10, wherein the first magnet comprises a handle that extends outwardly through the handle track.

12. The disposable wire holder of claim 1, wherein the first thin wire gripping layer comprises a thin rubber layer.

13. The disposable wire holder of claim 1, wherein the second thin wire gripping layer comprises a thin rubber layer.

* * * * *